United States Patent
Daum

(10) Patent No.: US 6,684,101 B2
(45) Date of Patent: Jan. 27, 2004

(54) IMPLANTABLE MEDICAL DEVICE EMPLOYING SINGLE DRIVE, DUAL SENSE IMPEDANCE MEASURING

(75) Inventor: Douglas R. Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 271 days.

(21) Appl. No.: 09/843,112

(22) Filed: Apr. 25, 2001

(65) Prior Publication Data

US 2002/0161310 A1 Oct. 31, 2002

(51) Int. Cl.[7] ................................................. A61B 5/05
(52) U.S. Cl. ....................... 600/547; 600/483; 600/484
(58) Field of Search ................................ 600/547, 481, 600/483–486, 506, 529, 508–510; 607/17, 18, 20, 24

(56) References Cited

U.S. PATENT DOCUMENTS

| | | | |
|---|---|---|---|
| 4,702,253 A | 10/1987 | Nappholz et al. | |
| 5,156,147 A | 10/1992 | Warren et al. | |
| 5,235,976 A | 8/1993 | Spinelli | |
| 5,284,136 A | 2/1994 | Hauck et al. | |
| 5,314,449 A | 5/1994 | Lindgren | |
| 5,318,597 A | 6/1994 | Hauck et al. | |
| 5,501,702 A | 3/1996 | Plicchi et al. | |
| 5,626,624 A | 5/1997 | Schaldach et al. | |
| 5,713,933 A | 2/1998 | Condie et al. | |
| 5,792,194 A | 8/1998 | Morra | |
| 5,817,136 A | * 10/1998 | Nappholz et al. | 607/17 |
| 5,824,019 A | 10/1998 | Rueter et al. | |
| 5,964,788 A | 10/1999 | Greenhut | |
| 6,070,100 A | 5/2000 | Bakels et al. | |
| 6,161,042 A | 12/2000 | Hartley et al. | |
| 6,415,183 B1 | * 7/2002 | Scheiner et al. | 607/42 |
| 6,445,951 B1 | * 9/2002 | Mouchawar | 607/28 |
| 6,459,929 B1 | * 10/2002 | Hopper et al. | 600/513 |
| 6,463,326 B1 | * 10/2002 | Hartley et al. | 607/20 |
| 2002/0002389 A1 | * 1/2002 | Bradley et al. | 607/8 |

* cited by examiner

Primary Examiner—Charles Marmor
(74) Attorney, Agent, or Firm—Crawford Maunu PLLC

(57) ABSTRACT

A method and system is implemented in an implantable medical device (IMD) and provides for the detection of multiple physiologic parameters in response to a single source current event. A high frequency source current signal is propagated through body tissues in the thorax, including the heart. The source current signal has a frequency greater than a frequency of a pacing current signal producible by the IMD. In response to the source current signal, a first voltage is detected between two portions of a first region of the heart substantially concurrently with sensing a second voltage between one of the IMD housing and a header/can electrode and one of the two portions of the first region of the heart. The first voltage is associated with a cardiac function and the second voltage is indicative of a respiratory function. The source current signal may be a single or multiple cycle current pulse. The source current signal may also be a continuous current signal. The source current signal may take the form of a monophasic current pulse or have a polyphasic character, such as in the case of a biphasic current pulse.

60 Claims, 6 Drawing Sheets

IMPLANTABLE MEDICAL DEVICE EMPLOYING SINGLE DRIVE, DUAL SENSE IMPEDANCE MEASURING

FIELD OF THE INVENTION

The present invention relates generally to implantable medical devices and, more particularly, to acquiring and processing multiple signals representative of several physiologic parameters associated with cardiac and respiratory functions.

BACKGROUND OF THE INVENTION

Various approaches have been developed for detecting certain physiologic parameters using trans-thoracic impedance measuring techniques. Such known approaches generally involve measuring changes in impedance between endocardial, subcutaneous or intrathoracic lead electrodes owing to the beating action of the heart, respiration or other physiologic activities. Measuring two physiologic parameters, for example, requires a expenditure of battery power in the form of current supplied during each impedance measurement in order to separately measure each of the physiologic parameters of interest. It is understood that a considerable percentage of battery life may be consumed for purposes of making necessary and investigatory transthoracic impedance measurements using conventional approaches.

One particular disadvantage of conventional transthoracic impedance measuring approaches results from inaccuracies that arise when discriminating between physiologic signals detected by impedance sensing techniques. Such known impedance sensing techniques are highly dependent on the geometrical path length and tissue inhomogeneities between source and sense electrodes. Measured physiologic signals are often highly modulated by the change in geometrical distance or electrical properties of tissue between two sense electrodes. This characteristic, which conventional approaches have attempted to address, has been found to reduce the accuracy of certain physiologic parameter measurements.

For the reasons stated above, and for other reasons stated below which will become apparent to those skilled in the art upon reading the present specification, there is a need in the art for improved trans-thoracic impedance measuring techniques for measuring a variety of physiologic parameters of interest. There exists a further need for such techniques that provide for reduced, rather than increased, battery power consumption. The present invention fulfills these and other needs.

SUMMARY OF THE INVENTION

The present invention is directed to a system and method implemented with an implantable medical device (IMD). In accordance with a broad characterization of the present invention, a high frequency source current signal is propagated through all or a portion of the body. A multiplicity of high frequency voltages are concurrently detected at a multiplicity of body locations in response to the high frequency source current signal. Each of the multiplicity of detected high frequency voltages is associated with a particular physiologic parameter. The locations of the detected high frequency voltages are judiciously selected to enhance detection of a particular physiologic parameter of interest. Physiologic voltages are extracted from the detected high frequency voltages, typically through use of a demodulation technique. A multiplicity of physiologic output signals are produced using the extracted physiologic voltages. The physiologic output signals may be used for a variety of purposes, including monitoring of numerous cardiac and respiratory function parameters, for example.

According to one embodiment of the present invention, parameters associated with cardiac function and/or respiratory function are derived using a single drive, dual sense impedance technique of the present invention. A multiplicity of sense voltages are concurrently acquired in response to a single source current event. In an alternative embodiment, a multiplicity of sense voltages are concurrently acquired in response to a continuous source current. The sense voltages are developed at particular locations of the heart and chest cavity that provide for enhanced detection of a particular physiologic components of interest. Although cardiac function and respiratory function represent two such physiologic components of interest, other physiologic functions associated with the pulmonary system or other systems of the human body may be advantageously evaluated using techniques of the present invention.

In accordance with one embodiment, an implantable medical device includes a housing and a header electrode, also referred to as a header indifferent electrode. It is understood that the housing may further include a can electrode rather than, or in addition to, a header electrode (e.g., a common header/can electrode). A high frequency source current signal is propagated through at least a portion of a heart. The source current signal has a frequency greater than a frequency of a pacing current signal producible by the IMD. The source current preferably has a frequency that avoids disturbance with a pacing function of the IMD (e.g., source current does not directly stimulate the heart).

In response to the source current signal, a first voltage is sensed between two portions of a first region of the heart substantially concurrently with sensing a second voltage between one of the IMD housing, header, and can electrode and one of the two portions of the first region of the heart. The first voltage, in the embodiment, is associated with a cardiac function and the second voltage is indicative of a respiratory function.

The source current signal may take several forms. For example, the source current signal may take the form of a single cycle current pulse or a multiple cycle current pulse. The source current signal may also be a continuous current signal. Further, the source current signal may take the form of a monophasic current pulse or have a polyphasic character, such as in the case of a biphasic current pulse.

By way of further example, the source current signal may be a multiple cycle current signal having a duration of between 1 and 10 cycles. The source current signal may also be a current signal having an amperage of between about 30 micro-amps and about 2 milli-amps. The source current signal typically has a frequency of between about 5 KHz and about 100 KHz.

The first and second voltages are typically high frequency voltages having respective frequencies equal to the frequency of the current signal. The first and second voltages are demodulated to develop first and second signals respectively associated with cardiac and respiratory functions. For example, the cardiac function of interest may be cardiac contraction or cardiac relaxation. Other parameters of cardiac function that may be indicated by the first signal include a flow of blood, volume of blood, or pressure of blood associated with the cardiac function. For example, the first signal may be indicative of a hemodynamic signal, such as a hemodynamic maximum sensor rate (HMSR) signal.

The second signal may, for example, be indicative of a rate, pattern, or depth of breathing associated with the respiratory function. By way of example, the second signal may be indicative of a ventilation signal, such as a minute ventilation signal.

In accordance with another embodiment of the present invention, a source current signal is propagated through at least a portion of a heart. In response to the source current signal, a first voltage is sensed between two portions of a first region of the heart. Concurrently with sensing of the first voltage and in response to the source current signal, a second voltage is sensed between one of the IMD housing, header, and can electrode and one of the two portions of the first region of the heart portion. A first signal indicative of a cardiac function is developed using the first voltage. A second signal indicative of a respiratory function is developed using the second voltage.

The source current signal may be introduced at one of the two portions of the first region of the heart portion. The first voltage may be a differential signal that is not referenced to the IMD housing. The first voltage may, for example, be sensed between two portions of a ventricle of the heart.

The first voltage may be developed between two electrodes of a common lead. Each electrode is coupled to a respective one of the two portions of the first region of the heart, typically in the right ventricle region. The first voltage is thus developed in the ventricle of the heart. The second voltage is sensed between one of the two electrodes in the ventricle and one of the IMD housing, header, and can electrode.

In accordance with another embodiment, an implantable medical device that implements a single drive, multiple sense methodology of the present invention includes a housing, a header electrode and/or a can electrode, and a current generator that produces a source current signal. A lead is coupled to the current generator. The lead includes a first electrode and a second electrode. The first and second electrodes are situated respectively at two portions of a first region of a heart. For example, the first and second electrodes may be ventricular electrodes. The source current signal is delivered to the heart via the first or second electrode.

A detector unit is coupled to the lead. The detector unit detects, in response to the source current signal, a first voltage between the first and second electrodes substantially concurrently with detecting a second voltage between one of the IMD housing, header, and can electrode and one of the first and second electrodes. The detector unit uses the first voltage to develop a first signal indicative of a cardiac function and uses the second voltage to develop a second signal indicative of a respiratory function.

In one configuration, the detector unit includes a first detector coupled to the lead that detects the first voltage and uses the first voltage to develop the first signal indicative of the cardiac function. The detector unit further includes a second detector coupled to the lead that detects the second voltage and uses the second voltage to develop the second signal indicative of the respiratory function.

The source current signal, as discussed previously, is typically a high frequency current signal having a frequency that avoids disturbance with a pacing function of the IMD. The source current signal, for example, is a high frequency current signal having a frequency greater than a frequency of a pacing current signal producible by the IMD. In this embodiment, the first and second voltages are high frequency voltages having respective frequencies equal to the frequency of the current signal. The detector unit includes a demodulator that demodulates the first and second voltages to respectively develop the first and second signals.

The lead may be a bipolar lead. The first electrode may be a tip electrode and the second electrode may be a ring electrode. In this arrangement, the first voltage is detected between the tip and ring electrodes of the lead. The second voltage is detected between one of the IMD housing, header, and can electrode and one of the tip and ring electrodes.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
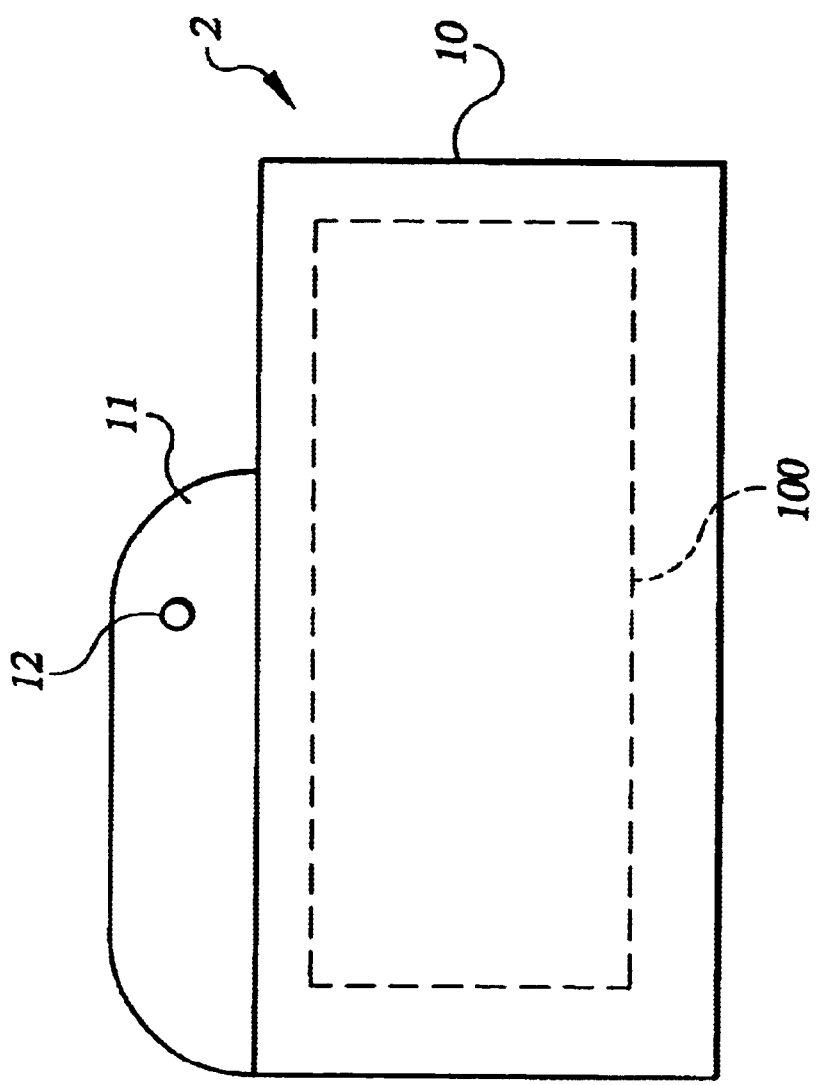
FIG. 1 shows a cardiac rhythm management device with which a single drive, dual sense impedance technique of the present invention may be implemented.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

A single drive, dual sense impedance technique of the present invention advantageously provides for improved physiologic signal measurements from impedance measuring circuitry within an implantable medical device (IMD), while minimizing battery energy drain. The circuitry and methodology of the present invention provides for improved accuracy when discriminating between physiologic signals detected by impedance sensing techniques without unreasonably increasing the energy drain of the IMD.

According to the present invention, multiple physiologic sense voltages are acquired in response to a single source current event, such as the propagation of a single or multiple cycle pulse source current into body tissues. In one embodiment, the source current may be a continuous current. It has been estimated that approximately two-thirds of the power consumption required to perform impedance measurements using conventional techniques is due to electrical current pulse generation.

Particularly in the case in which a pulse current is used as a source current according to the present invention, a significant reduction in IMD battery energy utilization may be achieved when performing trans-thoracic impedance measurements. For example, it has been estimated that a conventional impedance measuring technique that utilizes switched direction circuitry, for example, consumes about twice as much power as does a single drive, dual sense impedance technique of the present invention. Those skilled in the art will readily appreciate this reduction in power usage to perform trans-thoracic impedance measurements as significant.

Another advantage realized when implementing a single drive, dual sense impedance measuring technique of the present invention concerns increased accuracy of certain measured physiologic signals. Driving a current and sensing a voltage in response to such drive current between a ventricular lead and the housing of a pulse generator, for example, is highly dependent on the geometrical path length between the lead and the pulse generator. In other words, the voltage measured between the lead and the pulse generator is highly sensitive to the distance between the drive and sense electrodes. In this case, the measured physiologic signal is highly modulated by the change in geometrical distance between the two sense electrodes.

This characteristic is advantageous in certain cases, such as when using respiration sensors that depend on geometrical path length changes due to expansion and collapsing of the lungs. However, the time varying signal corresponding to cardiac function, such as contractions and relaxations, is more arbitrary, as the motion between the lead electrodes and the pace generator is often different from patient to patient.

A single drive, dual sense impedance measuring technique of the present invention provides for sensing of certain physiologic parameters by use of electrode configurations having a more steady or constant distance therebetween. An impedance measuring technique of the present invention also provides for concurrent sensing of various physiologic parameters by use of electrode configurations that allow for a varying geometrical path length between sense electrodes.

Referring to FIG. 1 there is diagrammatically shown a side view of a cardiac rhythm management device 2 with which a single drive, dual sense impedance measuring technique of the present invention may be implemented. It is understood that other implantable medical devices may be employed to implement the detection and analysis techniques of the present invention, such as defibrillator/cardioverter devices and cardiac monitors, for example. Accordingly, the following description of the present invention within the context of a cardiac rhythm management device is for illustrative purposes only, and is not to be regarded as limiting the scope of the present invention to such devices.

The cardiac rhythm management device 2 shown in FIG. 1 includes a conductive metal housing 10 and an insulating top or header 11. Mounted in the top 11 and isolated from the metal housing 10 is a button electrode 12, also referred to as a header electrode or header indifferent electrode in the art. The conductive metal housing 10 may further define a can electrode. Contained within the housing 10 is electronic circuit 100 which is explained in more detail below and which comprises the single drive, dual sense impedance measuring circuitry of the present invention.

Figure 2:
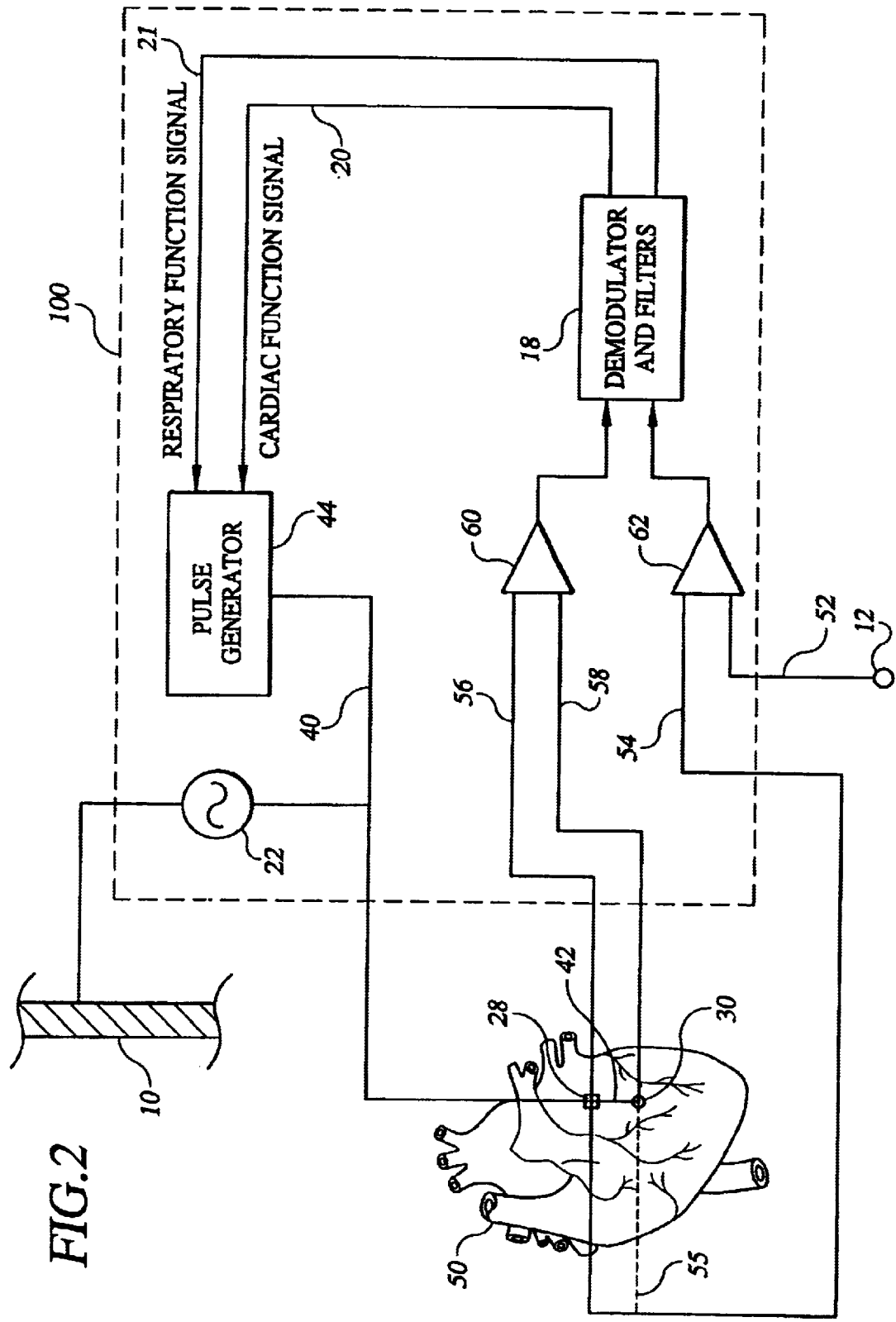
FIG. 2 is a schematic of a circuit with an implantable medical device that implements a single drive, dual sense impedance technique in accordance with an embodiment of the present invention.

Referring to FIGS. 1 and 2, the circuit 100 will now be described in greater detail. A pulse generator 44 which is contained within the housing or can 10 of the cardiac rhythm management device 2. An endocardial lead 40 is coupled to the pulse generator 44. The lead 40 is typically a bipolar lead as is known in the art. The lead 40 includes electrodes 28 and 30 located within one of the chambers of the heart 50. Electrode 30 may be, for example, a stimulating tip electrode on a catheter type lead while electrode 28 may be, for example, a ring electrode. Insulator lead body 42 mechanically supports electrodes 28 and 30. The tip and ring electrodes 30, 28 are typically separated by a approximately 10–25 mm.

An oscillator 22 is shown coupled to lead 40 and the housing 10. The oscillator 22 is arranged to produce an alternating source current signal at a frequency which is quite high compared to the heart rate. In general, the source current signal is sufficiently high so as not to adversely interfere with the normal cardiac monitoring and pacing functions of the cardiac rhythm management device 2. The frequency of the source current signal is generally in excess of 1 KHz, and is typically in the range from about 5 KHz to about 100 KHz. The source current signal may be a pulse current signal or a continuous current signal.

In the arrangement depicted in FIG. 2, the source current signal produced by oscillator 22 is driven by electrode 28 through body tissues and to the housing 10. Alternatively, the source current signal produced by oscillator 22 may be driven through body tissues by electrode 30 or other cardiac electrode of lead 40.

Monitoring of a respiratory function in response to a source current signal may be accomplished using several different sensing arrangements. In one arrangement, the ring electrode 28 is coupled to an input of differential amplifier 62 via conductor 54. Alternatively, the tip electrode 30 may be coupled to differential amplifier 62 via conductor 55, which is shown as a dashed line bridging to conductor 54 for illustrative purposes.

Another input of differential amplifier 62 is coupled to the header electrode 12 or the can electrode. Header electrode 12 typically has a surface area similar to that of ring electrode 28 and is disposed on the plastic top 11 of the implantable cardiac rhythm management device 2. In the embodiment shown in FIG. 2, the header electrode 12 is connected via lead 52 to differential amplifier 62. In an alternative arrangement, conductor 52 couples the input of differential amplifier 62 to the can or housing electrode, rather than to the header indifferent electrode 12.

Monitoring a cardiac function in response to a source current signal is accomplished using the tip and ring electrodes 30, 28. The ring electrode 28 is coupled to an input of differential amplifier 60 via conductor 56. The tip electrode 30 is coupled to another input of differential amplifier 60 via conductor 58. It is understood that conductors 52, 54, 56, and 58 are typically conductors of lead 40, and may be the same conductor.

Differential amplifiers 60 and 62 are typically sense amplifiers of a design and sensitivity as is known in the art.

In embodiments in which detection of more than two physiologic vectors is desired, an additional sense amplifier is typically needed to detect each such additional vector. Although the addition of a sense amplifier to detect each additional vector does increase the number of components of circuitry 100, the battery power savings resulting from measuring trans-thoracic impedance variations according to the present invention far exceeds the power required by such additional sense amplifier.

The output of differential amplifier 62 is coupled to a demodulator and filtering circuit 18. The output of differential amplifier 60 is also coupled to demodulator and filtering circuit 18. The demodulator and filtering circuit 18 is coupled by conductors 20 and 21 to the pulse generator 44. Conductor 20 communicates a cardiac function signal from demodulator and filtering circuit 18 to pulse generator 44, while conductor 21 communicates a respiratory function signal from demodulator and filtering circuit 18 to pulse generator 44.

The demodulator and filtering circuit 18 includes signal processing circuits, such as those disclosed in U.S. Pat. Nos. 4,686,987, 5,284,136, and 5,318,597, which are hereby incorporated herein by reference. Demodulator and filtering circuit 18 also includes filtering circuitry that separates the higher frequency cardiac function signals from the lower frequency respiratory function signals, such as that shown in U.S. Pat. No. 5,137,019, which is hereby incorporated herein by reference.

As an example of one illustrative pacing operation, the pulse generator 44 provides stimulating pulses to stimulating electrodes in a known manner to pace the heart. Electrodes 28 and 12 sense electrical impedance variations in the thoracic cavity, which may be due to the pumping action of the heart or other physiological function of interest. The signals sensed by electrodes 28 and 12 are fed into the differential sense amplifier 62 which provides a differential signal to the demodulator and filtering circuit 18.

The demodulator and filtering circuit 18 includes circuitry for demodulating the modulated carrier signal and recovering the modulating envelope signal therefrom, as is known in the art. The modulating signal contains frequency components proportional to certain physiologic parameters, such as instantaneous stroke volume or cardiac contraction of the patient's heart and instantaneous tidal volume of the patient's ventilation. The demodulator and filtering circuit 18 then provides appropriate control signals to the pulse generator after processing the modulating signal. The pulse generator responds to the control signal by, for example, determining a rate at which the heart stimulating pulses will be generated.

Figure 3:
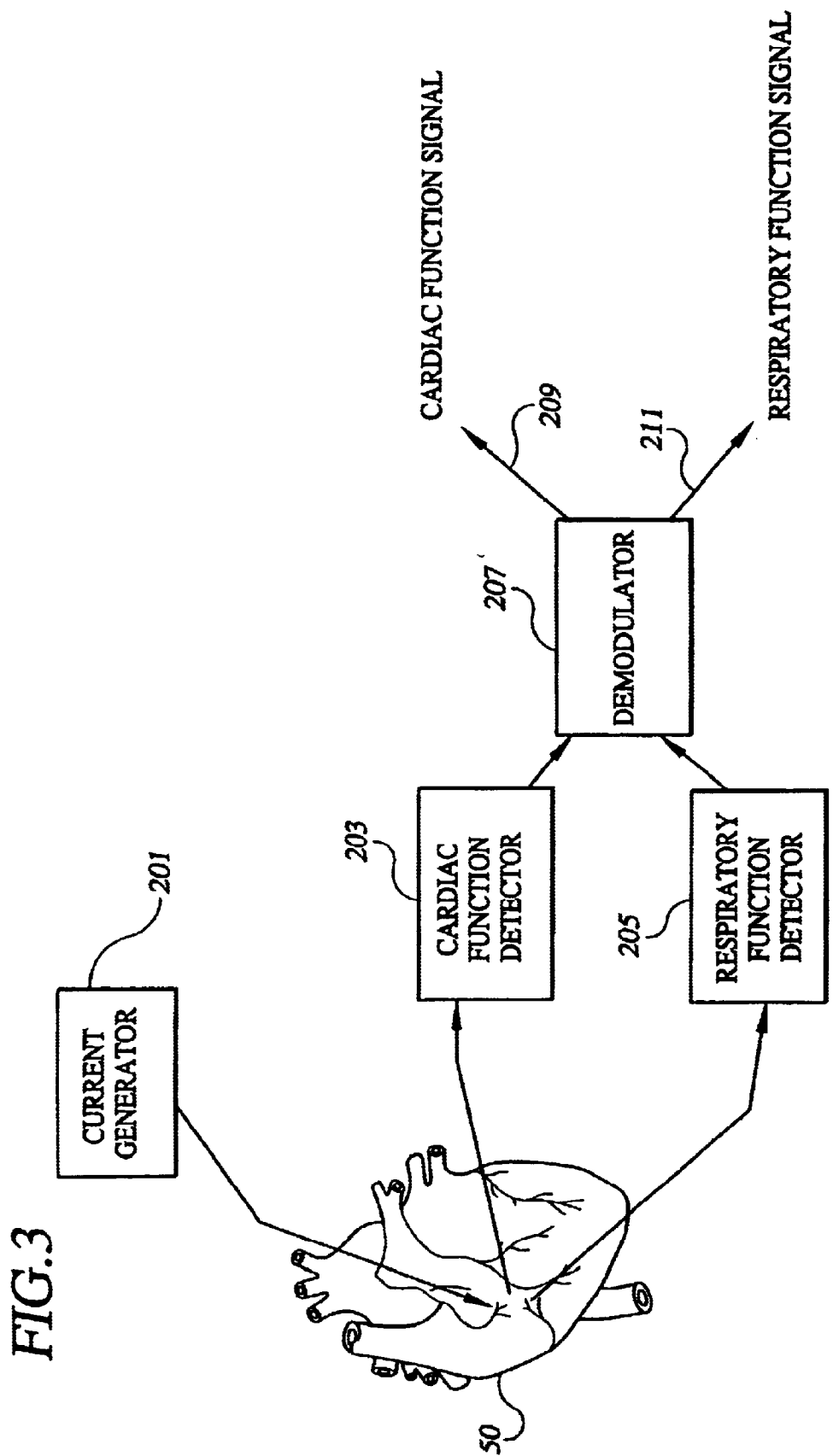
FIG. 3 illustrates a block diagram of several components of an implantable medical device that implements a single drive, dual sense impedance technique in accordance with an embodiment of the present invention.

Additional functionality provided by the circuitry of FIG. 2 for implementing a single drive, dual sense impedance measuring technique of the present invention will now be described. FIG. 3 illustrates an embodiment of the present invention which includes a current generator 201 that generates a high frequency source current signal. The source current signal may take several forms, such as a single cycle current pulse or a multiple cycle current pulse. The source current signal may also be a continuous current signal. Further, the source current signal may take the form of a monophasic current pulse or have a polyphasic character, such as in the case of a biphasic current pulse.

By way of further example, the source current signal may be a multiple cycle current signal having a duration of between 1 and 10 cycles. The source current signal may also be a current signal having an amperage of between about 30 micro-amps and about 2 milli-amps. The source current signal typically has a frequency of between about 5 KHz and about 100 KHz. For example, the source current signal may be a pulsed 2-cycle 25 KHz square wave. The pulse source current signal may be propagated several times per second, such as between 10 and 100 times per second.

The high frequency source current signal is propagated through body tissues, including, in particular, the heart 50. A respiratory function detector 205 detects a physiologic parameter indicative of a respiratory function of the patient. The respiratory function detector 205 may, for example, detect physiologic voltages indicative of a rate, pattern, or depth of breathing associated with the respiratory function. One such physiologic voltage of interest may be a voltage indicative of a ventilation signal. The detected respiratory-related high frequency voltage signal is communicated from the respiratory function detector 205 to a demodulator 207. Demodulator 207, which typically performs various signal processing and filtering functions as is known in the art, extracts the information signal component from the high frequency carrier and provides a respiratory function signal 211 at its output.

By way of example, and referring again to FIG. 2, an alternating source current drive signal having a frequency of about 5 KHz or more and an amplitude which is sufficiently low to preclude capture is propagated between the tip or ring electrode 30, 28 of lead 40 and the metal can comprising the cardiac rhythm management device's housing 10. As shown in FIG. 2, the ring electrode 28 on lead 40 and the header indifferent electrode 12 disposed on the cardiac rhythm management device's insulating lead socket 11 are connected to sense amplifier 62.

Breathing activity of the patient, as well as systolic events and other motion artifacts, combine to modulate the alternating source current signal. A modulated responsive voltage signal is detected between the ring and header/can electrodes 28, 12 and fed into demodulator and filtering circuitry 18 whose output is an analog representation of the envelope (i.e., information component of the modulated voltage signal) which remains when the high frequency carrier is removed. The respiratory function signal is communicated to pulse generator 44 via conductor 21.

Minute ventilation is one such respiratory-related parameter that has been found to closely correlate with physical exercise and, therefore, metabolic demand. Minute ventilation may be defined as the volume of air inspired and expired during a predetermined time period. It has been found experimentally that minute ventilation tracks very well with metabolic need over a range of heart rates and, therefore, provides a good index for a rate adaptive cardiac rhythm management device, provided that the technique used to derive the MV signal is not contaminated by events other than respiratory activity.

Referring again to FIG. 3, a cardiac function detector 203 detects a physiologic signal related to cardiac function in response to the source current signal. For example, the cardiac function of interest may be cardiac contraction or cardiac relaxation. Other parameters of cardiac function that may be indicated by the signal detected by cardiac function detector 203 include a flow of blood, volume of blood, or pressure of blood associated with cardiac function. One such physiologic parameter of interest may be a hemodynamic parameter indicative of the filling interval of the heart. The detected cardiac or circulatory-related high frequency voltage signal is communicated from the cardiac function detector 203 to demodulator 207. Demodulator 207 extracts the information signal component from the high frequency carrier and provides a cardiac function signal 209 at its output.

A hemodynamic parameter may be used, for example, in a technique for measuring the total active time of a cardiac cycle, where the total active time represents the total time elapsing between a ventricular pacing pulse or a sensed R-wave and the end of the filling phase of the ventricles when the ventricles are being filled at their "fast-filling rate." The measured total active time may then be processed in accordance with an algorithm for producing a control signal which is proportional to the measured value. This control signal may then be applied to a variable rate pulse generator (e.g., pulse generator 44 shown in FIG. 2) for controlling the rate at which the cardiac stimulating pulses are produced or for establishing a hemodynamically determined upper rate limit for a rate adaptive cardiac rhythm management device.

The total active time parameter value can be determined, for example, by utilizing an impedance versus time signal obtained utilizing a known impedance plethysmography technique, such as that disclosed in U.S. Pat. Nos. 5,235,976 and 4,686,987, which are hereby incorporated herein in their respective entireties, by extrapolating a line extending through two points in the fast-filling phase of the impedance curve to the point where that line reaches the minimum impedance level determined in the same beat. The total active time is determined as the interval starting with a natural or paced beat and ending with the point where that linear regression line reaches the end-diastolic impedance from the previous beat.

Hemodynamic stability may thus be maintained by insuring that a stimulating pulse does not occur during the patient's active time. It should be understood that if insufficient time is allowed for the heart to fill at the maximum filling rate, i.e., pacing during the fast-filling phase, proper cardiac output cannot be sustained.

Figure 4:
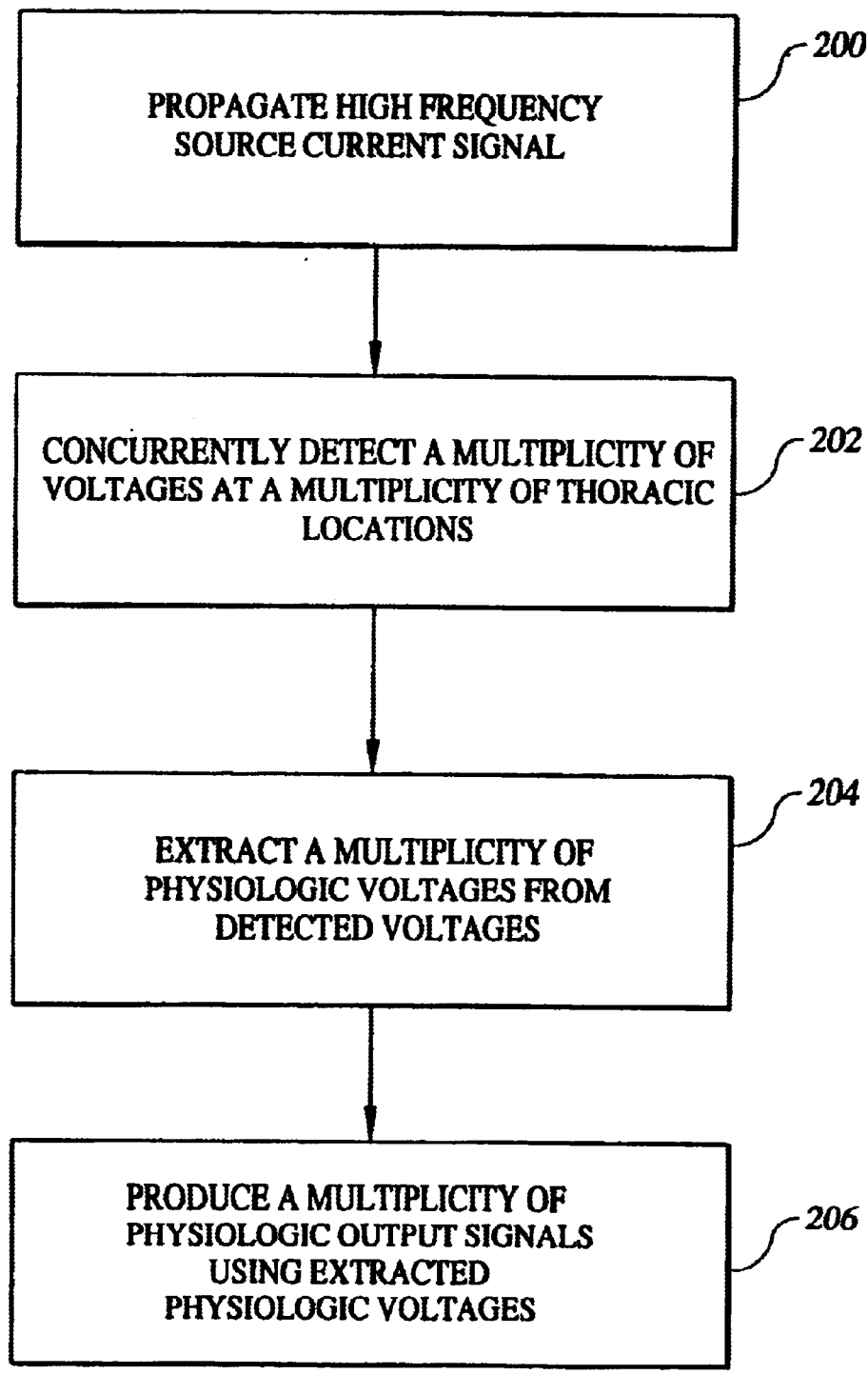
FIG. 4 illustrates several processes of a single drive, dual sense impedance technique in accordance with an embodiment of the present invention.
Figure 5:
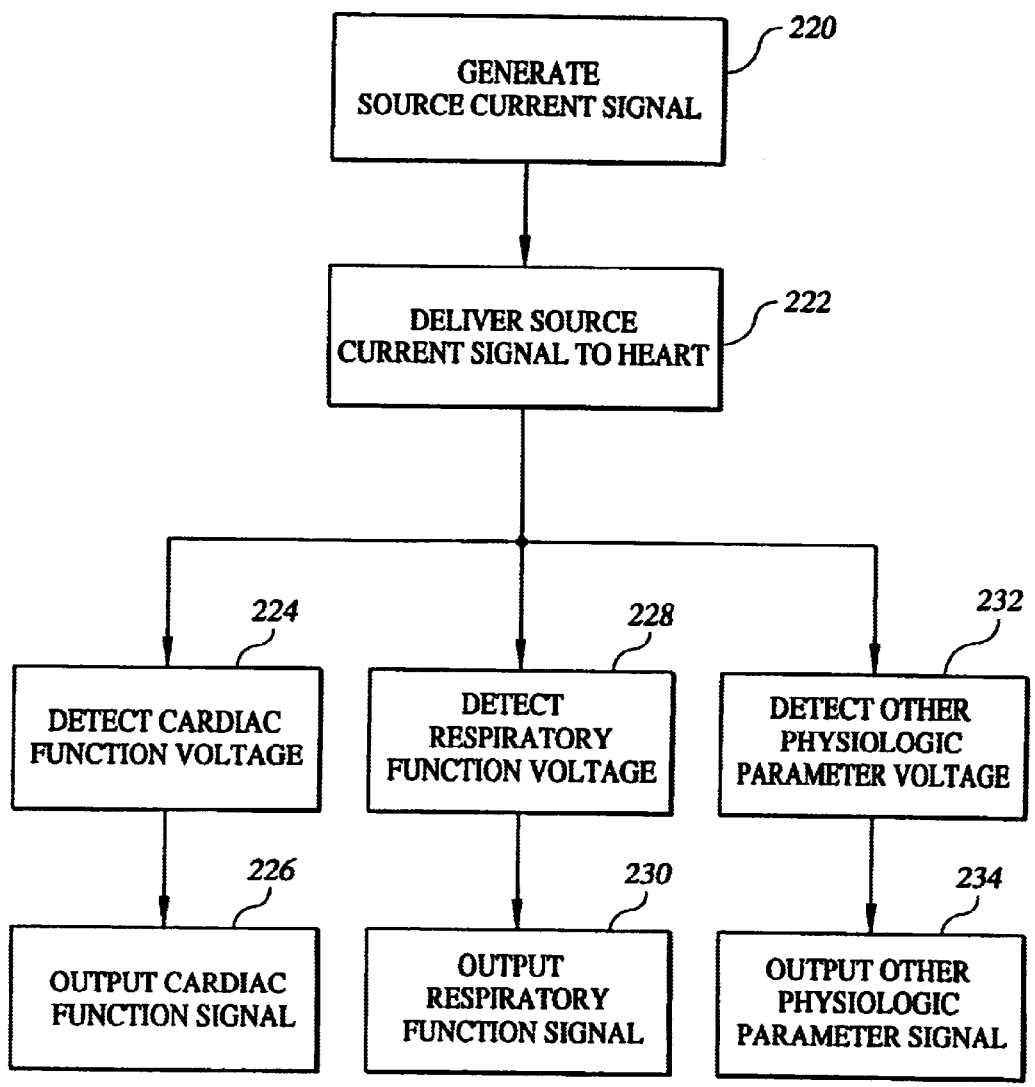
FIG. 5 illustrates several processes of a single drive, dual sense impedance technique in accordance with another embodiment of the present invention.
Figure 6:
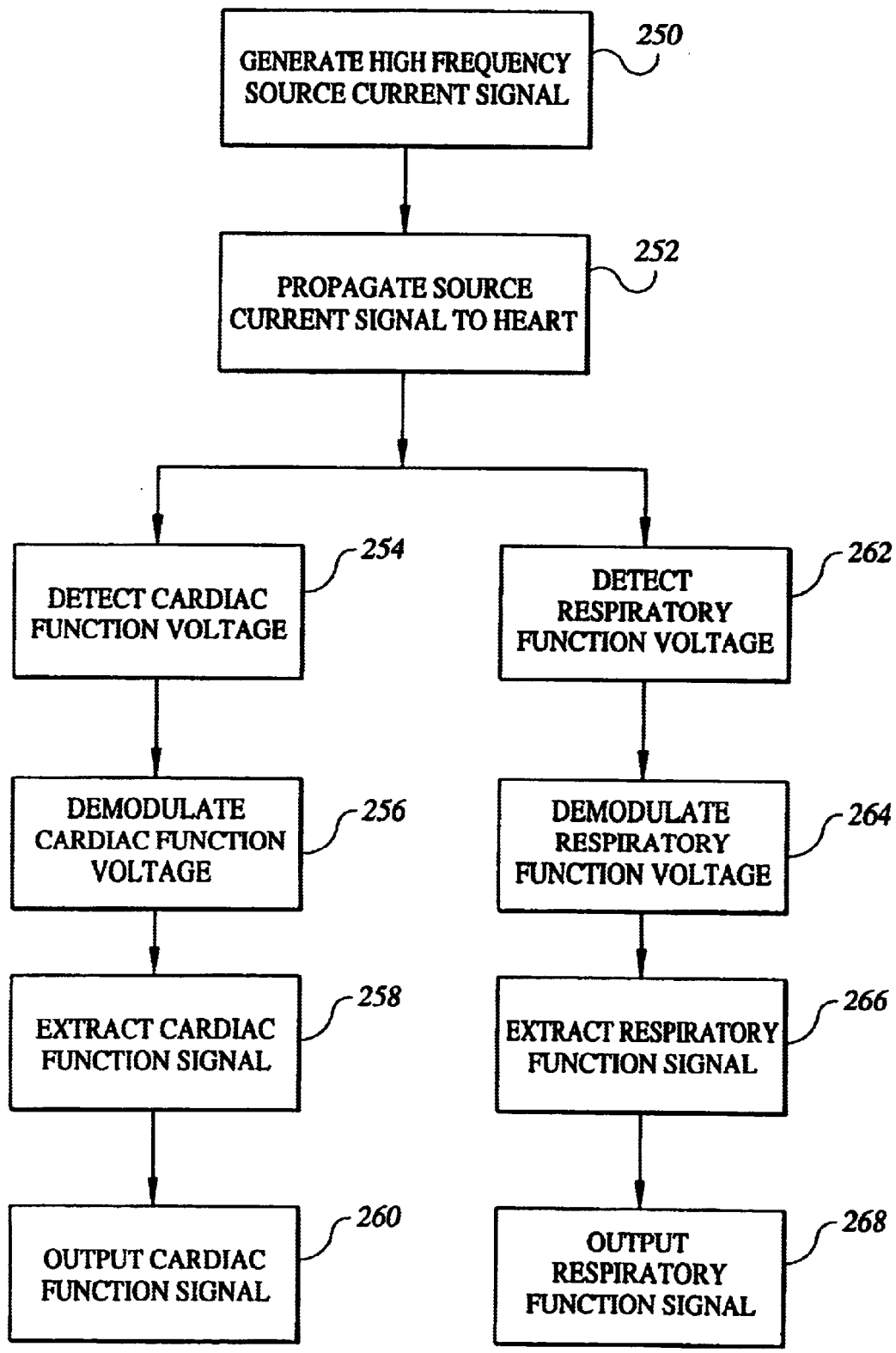
FIG. 6 illustrates several processes of a single drive, dual sense impedance technique in accordance with a further embodiment of the present invention.

Turning now to FIGS. 4–6, there is illustrated several flow diagrams that describe various processes of a single drive, dual sense impedance technique of the present invention. The methodologies shown in FIGS. 4–6 may be implemented using IMD circuitry described hereinabove. It is understood, however, that the techniques and methods described herein may be implemented in implantable medical devices having configurations and functionality differing from that described hereinabove.

In accordance with one embodiment of the present invention, and with particular reference to FIG. 4, a high frequency source current signal is propagated 200 through body tissues. A multiplicity of voltages is concurrently detected 202 at a multiplicity of thoracic locations. Each of the thoracic locations is associated with a physiologic parameter of interest that is predominate over other detectable physiologic parameters at that location. A multiplicity of physiologic voltages are extracted 204 using the detected voltages. The detected voltages have a frequency equal to that of the source current signal. A multiplicity of physiologic output signals are produced 206 using the extracted physiologic voltages.

FIG. 5 illustrates another embodiment of a single drive, dual sense impedance technique of the present invention. According to this embodiment, a source current signal is generated 220 and delivered 222 to the heart and other body tissues via a trans-thoracic pathway. In response to the source current signal, several physiologic voltages are detected substantially concurrently. It is understood that the term "concurrently" as using in this context takes into account the slight propagation delay of the source current signal in reaching detection locations in the body having differing geometrical path lengths with respect to the source of source current signal propagation.

As shown in FIG. 5, a cardiac function voltage (e.g., a hemodynamic signal voltage) is detected 224 concurrently with detection 228 of a respiratory function voltage (e.g., MV voltage) in response to the delivered source current signal. Other physiologic parameter voltages may also be detected 232 concurrently with the cardiac and respiratory function voltages. Output cardiac and respiratory function signals are output 226, 230, respectively, as are any other physiologic parameter signals 234. These output signals may be used for a variety of purposes, including pacing and defibrillating purposes.

FIG. 6 illustrates a further embodiment of a single drive, dual sense impedance technique of the present invention. According to this embodiment, a high frequency source current signal is generated 250 and propagated 252 through the heart and other body tissues via a trans-thoracic pathway. Voltages relating to a cardiac function and respiratory function are respectively detected 254, 262 substantially concurrently. The detected cardiac and respiratory-related voltages are respectively demodulated 256, 264 to extract 258, 266 the information content of these high frequency voltage signals from their carriers. The extracted cardiac and respiratory function signals are respectively output 260, 268, such as for use by a pace generator of a cardiac rhythm management device device, for example.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method implemented with an implantable medical device (IMD) comprising a housing and a header or can electrode, the method comprising:

propagating a source current signal through at least a portion of a heart;

sensing, in response to the source current signal, a first voltage between two portions of a first region of the heart portion;

sensing, concurrently with sensing of the first voltage and in response to the source current signal, a second voltage between one of the IMD housing and header/can electrode and one of the two portions of the first region of the heart portion;

developing a first signal indicative of a cardiac function using the first voltage; and developing a second signal indicative of a respiratory function using the second voltage.

2. The method of claim 1, wherein the source current signal comprises a single cycle current pulse.

3. The method of claim 1, wherein the source current signal comprises a multiple cycle current pulse.

4. The method of claim 1, wherein the source current signal comprises a monophasic current pulse.

5. The method of claim 1, wherein the source current signal comprises a biphasic current pulse.

6. The method of claim 1, wherein the source current signal comprises a continuous current signal.

7. The method of claim 1, wherein the source current signal comprises a multiple cycle current signal having a duration of between 1 and 10 cycles.

8. The method of claim 1, wherein the source current signal comprises a current pulse having an amperage of between about 30 micro-amps and about 2 milli-amps.

9. The method of claim 1, wherein the source current signal comprises a current signal having a frequency that avoids disturbance with a pacing function of the IMD.

10. The method of claim 1, wherein the source current signal comprises a current signal having a frequency greater than a frequency of a pacing current signal producible by the IMD.

11. The method of claim 1, wherein the source current signal comprises a current signal having a frequency of between about 5 KHz and about 100 KHz.

12. The method of claim 1, wherein propagating the source current signal comprises introducing the source current signal at one of the two portions of the first region of the heart portion.

13. The method of claim 1, wherein the first voltage comprises a differential signal that is not referenced to the IMD housing.

14. The method of claim 1, wherein the first voltage comprises a voltage between two portions of a ventricle of the heart.

15. The method of claim 1, wherein the first voltage comprises a voltage developed between two electrodes of a common lead, each electrode coupled to a respective one of the two portions of the first region of the heart portion.

16. The method of claim 1, wherein the one of the two portions of the first region comprises a portion of the ventricle of the heart, and the second voltage comprises a voltage between the portion of the ventricle and one of the IMD housing and header/can electrode.

17. The method of claim 1, wherein the second voltage comprises a voltage developed between one of a plurality of electrodes of a common lead and one of the IMD housing and header/can electrode, wherein each electrode is coupled to a respective one of the two portions of the first region of the heart portion.

18. The method of claim 1, wherein the first signal comprises a hemodynamic signal.

19. The method of claim 1, wherein the second signal comprises a minute ventilation signal.

20. The method of claim 1, wherein the cardiac function comprises cardiac contraction or cardiac relaxation.

21. The method of claim 1, wherein the first signal is indicative of a flow of blood, volume of blood, or pressure of blood associated with the cardiac function.

22. The method of claim 1, wherein the second signal is indicative of a rate, pattern, or depth of breathing associated with the respiratory function.

23. An implantable medical device (IMD) comprising a housing and a header or can electrode, the IMD comprising:
   a current generator, the current generator producing a source current signal;
   a lead coupled to the current generator, the lead comprising a first electrode and a second electrode, the first and second electrodes situated respectively at two portions of a first region of a heart, the source current signal delivered to the heart via the first or second electrode; and
   a detector unit coupled to the lead, the detector unit detecting, in response to the source current signal, a first voltage between the first and second electrodes substantially concurrently with detecting a second voltage between one of the IMD housing and header/can electrode and one of the first and second electrodes, the detector unit using the first voltage to develop a first signal indicative of a cardiac function and using the second voltage to develop a second signal indicative of a respiratory function.

24. The device of claim 23, wherein the detector unit further comprises:
   a first detector coupled to the lead that detects the first voltage and uses the first voltage to develop the first signal indicative of the cardiac function; and
   a second detector coupled to the lead that detects the second voltage and uses the second voltage to develop the second signal indicative of the respiratory function.

25. The device of claim 23, wherein the source current signal comprises a high frequency current signal having a frequency that avoids disturbance with a pacing function of the IMD.

26. The device of claim 25, wherein:
   the source current signal comprises a high frequency current signal having a frequency greater than a frequency of a pacing current signal producible by the IMD;
   the first and second voltages comprise high frequency voltages having respective frequencies equal to the frequency of the current signal; and
   the detector unit comprises a demodulator that demodulates the first and second voltages to respectively develop the first and second signals.

27. The device of claim 23, wherein the lead comprises a bipolar lead.

28. The device of claim 23, wherein the first electrode comprises a tip electrode and the second electrode comprises a ring electrode, and the first voltage is detected between the tip and ring electrodes of the lead.

29. The device of claim 28, wherein the second voltage is detected between one of the IMD housing and header/can electrode and one of the tip and ring electrodes.

30. The device of claim 23, wherein the source current signal comprises a single cycle current pulse.

31. The device of claim 23, wherein the source current signal comprises a multiple cycle current pulse.

32. The device of claim 23, wherein the source current signal comprises a monophasic current pulse.

33. The device of claim 23, wherein the source current signal comprises a biphasic current pulse.

34. The device of claim 23, wherein the source current signal comprises a continuous current signal.

35. The device of claim 23, wherein the source current signal comprises a multiple cycle current signal having a duration of between 1 and 10 cycles.

36. The device of claim 23, wherein the source current signal comprises a current pulse having an amperage of between about 30 micro-amps and about 2 milli-amps.

37. The device of claim 23, wherein the source current signal comprises a current signal having a frequency of between about 5 KHz and about 100 KHz.

38. The device of claim 23, wherein the first and second electrodes comprise ventricular electrodes.

39. The device of claim 23, wherein the first signal comprises a hemodynamic signal.

40. The device of claim 23, wherein the second signal comprises a minute ventilation signal.

41. The device of claim 23, wherein the cardiac function comprises cardiac contraction or cardiac relaxation.

42. The device of claim 23, wherein the first signal is indicative of a flow of blood, volume of blood, or pressure of blood associated with the cardiac function.

43. The device of claim 23, wherein the second signal is indicative of a rate, pattern, or depth of breathing associated with the respiratory function.

44. A method implemented with an implantable medical device (IMD) comprising a housing and a header or can electrode, the method comprising:

propagating a high frequency source current signal through at least a portion of a heart, the source current signal having a frequency greater than a frequency of a pacing current signal producible by the IMD; and sensing, in response to the source current signal, a first voltage between two portions of a first region of the heart portion substantially concurrently with sensing a second voltage between one of the IMD housing and header/can electrode and one of the two portions of the first region of the heart portion, the first voltage associated with a cardiac function and the second voltage indicative of a respiratory function.

45. The method of claim 44, wherein the source current signal comprises a single cycle current pulse.

46. The method of claim 44, wherein the source current signal comprises a multiple cycle current pulse.

47. The method of claim 44, wherein the source current signal comprises a continuous current signal.

48. The method of claim 44, wherein the source current signal comprises a current signal having a frequency of between about 5 KHz and about 100 KHz.

49. The method of claim 44, wherein the first and second voltages comprise high frequency voltages having respective frequencies equal to the frequency of the current signal, the method further comprising demodulating the first and second voltages to develop respective first and second signals, the first and second signals associated with the cardiac and respiratory functions, respectively.

50. The method of claim 44, wherein the cardiac function comprises cardiac contraction or cardiac relaxation.

51. The method of claim 44, wherein the first signal is indicative of a flow of blood, volume of blood, or pressure of blood associated with the cardiac function.

52. The method of claim 44, wherein the second signal is indicative of a rate, pattern, or depth of breathing associated with the respiratory function.

53. A method for detecting a physiological condition using an implantable medical device, comprising:

propagating a source current signal through at least a portion of a heart;

sensing, in response to the source current signal, a first voltage between two portions of a first region of the heart portion; and sensing, concurrently with sensing the first voltage and in response to the source current signal, a second voltage between one of the IMD housing and header/can electrode and one of the two portions of the first region of the heart portion, the first voltage indicative of a cardiac function other than a pacing response and the second voltage indicative of a respiratory function.

54. The method of claim 53, wherein the source current signal comprises a current signal having a frequency that avoids disturbance of cardiac pacing.

55. The method of claim 53, wherein the first and second voltages comprise high frequency voltages having respective frequencies equal to the frequency of the current signal, the method further comprising demodulating the first and second voltages to develop respective first and second signals, the first and second signals associated with the cardiac and respiratory functions, respectively.

56. The method of claim 53, wherein the source current signal comprises a multiple cycle current pulse.

57. The method of claim 53, wherein the source current signal comprises a single cycle current pulse.

58. The method of claim 53, wherein the source current signal comprises a monophasic current pulse.

59. The method of claim 53, wherein the source current signal comprises a multiphasic current pulse.

60. The method of claim 53, wherein the first voltage comprises a differential signal that is not referenced to a housing of the implantable medical device.

* * * * *